US008051700B2

(12) United States Patent  (10) Patent No.: US 8,051,700 B2
Wang et al.  (45) Date of Patent: Nov. 8, 2011

(54) EXHAUST GAS SENSOR AND METHOD FOR DETERMINING CONCENTRATIONS OF EXHAUST GAS CONSTITUENTS

(75) Inventors: Da Yu Wang, Troy, MI (US); Walter T. Symons, Grand Blanc, MI (US); Robert J. Farhat, Grosse Pointe Park, MI (US); Sheng Yao, Macomb, MI (US)

(73) Assignee: Delphi Technologies, Inc., Troy, MI (US)

( * ) Notice: Subject to any disclaimer, the term of this patent is extended or adjusted under 35 U.S.C. 154(b) by 528 days.

(21) Appl. No.: 12/240,354

(22) Filed: Sep. 29, 2008

(65) Prior Publication Data

US 2010/0077833 A1  Apr. 1, 2010

(51) Int. Cl.
*G01N 7/00* (2006.01)

(52) U.S. Cl. ....................................................... 73/23.31

(58) Field of Classification Search ........................ None
See application file for complete search history.

(56) References Cited

U.S. PATENT DOCUMENTS

| | | | |
|---|---|---|---|
| 4,770,760 A | 9/1988 | Noda et al. |
| 4,927,517 A | 5/1990 | Mizutani et al. |
| 5,145,566 A | 9/1992 | Logothetis et al. |
| 6,153,071 A | 11/2000 | Omara et al. |
| 6,224,727 B1 | 5/2001 | Miyata et al. |
| 6,544,405 B2 | 4/2003 | Clyde et al. |
| 6,555,159 B2 | 4/2003 | Clyde et al. |
| 6,689,266 B2 | 2/2004 | Kato et al. |
| 7,074,319 B2 | 7/2006 | Wang et al. |
| 7,294,252 B2 | 11/2007 | Wang et al. |
| 7,422,052 B2 | 9/2008 | Reyzin et al. |
| 7,964,072 B2 | 6/2011 | Wang et al. |
| 2001/0025786 A1* | 10/2001 | Hasei et al. ................... 204/424 |
| 2007/0079597 A1 | 4/2007 | Wang et al. |
| 2007/0080074 A1 | 4/2007 | Wang et al. |
| 2007/0100995 A1 | 5/2007 | Isenmann et al. |
| 2008/0230385 A1 | 9/2008 | Lankheet et al. |
| 2009/0266142 A1* | 10/2009 | Wang et al. ................... 73/23.32 |

(Continued)

FOREIGN PATENT DOCUMENTS

DE  10027900 A1  12/2001

(Continued)

OTHER PUBLICATIONS

David B. Quinn, Earl W. Lankheet, Kenneth Howden, NOx Sensor for Direct Injection Emission Control, Combustion and Emission Control for Advanced CIDI Engines FY 2002 Progress Report, 93-97.

(Continued)

*Primary Examiner* — Hezron E Williams
*Assistant Examiner* — Alex Devito
(74) *Attorney, Agent, or Firm* — Thomas N. Twomey

(57) ABSTRACT

An exhaust gas sensor and a method for determining concentrations of exhaust gas constituents are provided. The exhaust gas sensor includes a $NO_2$ Nernst cell that generates a first voltage indicative of a $NO_2$ concentration in the exhaust gases communicating with the $NO_2$ sensing electrode. The exhaust gas sensor further includes a $NO_x$ Nernst cell that generates a second voltage indicative of a $NO_x$ concentration in the exhaust gases communicating with the $NO_x$ sensing electrode. The exhaust gas sensor further includes a $NH_3$ Nernst cell that generates a third voltage indicative of a $NH_3$ concentration in the exhaust gases communicating with the $NH_3$ sensing electrode.

6 Claims, 3 Drawing Sheets

U.S. PATENT DOCUMENTS

2010/0032292 A1  2/2010  Wang et al.

FOREIGN PATENT DOCUMENTS

WO  WO2007014388  2/2007

OTHER PUBLICATIONS

David B. Quinn, Earl W. Lankheet, Roland Gravel, NOx Sensor for Direct Injection Emission Control, Advanced Combustion Engine R&D FY 2003 Progress Report, 159-164.

Michael Pollard, Craig Habeger, Paul Park, Amy Fluharty, John Fairbanks, Development of Metal Substrate for DeNOx Catalysts and Particulate Traps, Advanced Combustion Engine R&D FY 2004 Progress Report, 229-256.

David B. Quinn, Earl W. Lankheet, Roland Gravel, NOx Sensor for Direct Injection Emission Control, Advanced Combustion Engine Technologies FY 2005 Progress Report, 243-258.

U.S. Appl. No. 11/839,340, filed Aug. 15, 2007 entitled: Oxygen Sensor and Method for Manufacturing the Oxygen Sensor.

U.S. Appl. No. 12/056,789, filed Mar. 27, 2008 entitled: Exhaust Gas Sensing System and Methods for Sensing Concentrations of Exhaust Gas Constituents.

U.S. Appl. No. 12/109,405, filed Apr. 25, 2008 entitled: Systems and Methods for Sensing an Ammonia Concentration in Exhaust Gases.

Rule 132 Declaration by Da Yu Wang originally submitted Jan. 10, 2011 in prosecution of U.S. Appl. No. 12/245,248.

* cited by examiner

EXHAUST GAS SENSOR AND METHOD FOR DETERMINING CONCENTRATIONS OF EXHAUST GAS CONSTITUENTS

BACKGROUND

A $NO_x$ sensor has been developed that detects $NO_x$ concentrations. However, the $NO_x$ sensor is not capable of directly determining nitrogen dioxide ($NO_2$) concentrations. Further, the $NO_x$ sensor may not be able to determine $NO_x$ concentrations in exhaust gases when the exhaust gases have ammonia ($NH_3$) therein.

Accordingly, the inventors herein have recognized a need for an improved exhaust gas sensor that minimizes and/or eliminates the above-mentioned deficiencies.

SUMMARY OF THE INVENTION

An exhaust gas sensor in accordance with an exemplary embodiment is provided. The exhaust gas sensor includes a $NO_2$ Nernst cell having a $NO_2$ sensing electrode and a first reference electrode. The first reference electrode communicates with exhaust gases in a first chamber. The $NO_2$ sensing electrode communicates with exhaust gases passing through a porous layer. The $NO_2$ Nernst cell generates a first voltage indicative of a $NO_2$ concentration in the exhaust gases communicating with the $NO_2$ sensing electrode. The exhaust gas sensor further includes a $NO_x$ Nernst cell having a $NO_x$ sensing electrode and the first reference electrode. The $NO_x$ sensing electrode communicates with the exhaust gases passing through the porous layer. The $NO_x$ Nernst cell generates a second voltage indicative of a $NO_x$ concentration in the exhaust gases communicating with the $NO_x$ sensing electrode. The exhaust gas sensor further includes a $NH_3$ Nernst cell having a $NH_3$ sensing electrode and the first reference electrode. The $NH_3$ sensing electrode communicates with the exhaust gases passing through the porous layer. The $NH_3$ Nernst cell generates a third voltage indicative of a $NH_3$ concentration in the exhaust gases communicating with the $NH_3$ sensing electrode.

A method for determining concentrations of exhaust gas constituents in accordance with another exemplary embodiment is provided. The method includes generating a first voltage indicative of a $NO_2$ concentration in exhaust gases communicating with the $NO_2$ sensing electrode of a $NO_2$ Nernst cell, utilizing the $NO_2$ Nernst cell. The $NO_2$ Nernst cell further has a first reference electrode communicating the exhaust gases in a first chamber. The method further includes generating a second voltage indicative of a $NO_x$ concentration in exhaust gases communicating with the $NO_x$ sensing electrode of a $NO_x$ Nernst cell, utilizing the $NO_x$ Nernst cell. The $NO_x$ Nernst cell further has the first reference electrode. The method further includes generating a third voltage indicative of a $NH_3$ concentration in exhaust gases communicating with a $NH_3$ sensing electrode of a $NH_3$ Nernst cell, utilizing the $NH_3$ Nernst cell. The $NH_3$ Nernst cell further has the first reference electrode.

DETAILED DESCRIPTION OF EXEMPLARY EMBODIMENTS

Figure 1:
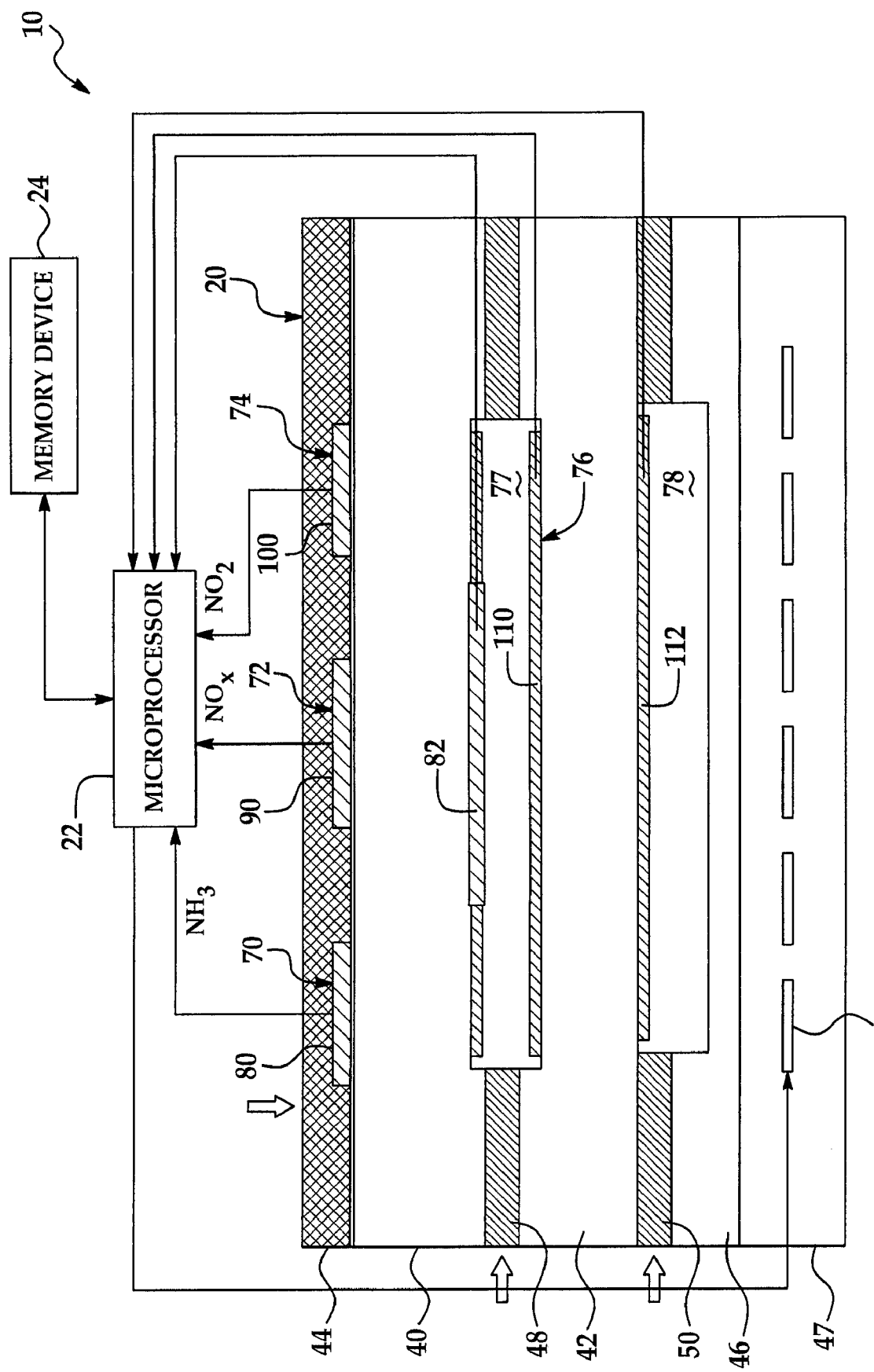
FIG. 1 is a schematic of an exhaust gas sensing system having an exhaust gas sensor in accordance with an exemplary embodiment.

Referring to FIG. 1, a system 10 for sensing concentrations of exhaust gas constituents in accordance with an exemplary embodiment is provided. The system 10 includes an exhaust gas sensor 20, a microprocessor 22, and a memory device 24. An advantage of the system 10 is that the system 10 can accurately detect a $NO_x$ concentration, a $NO_2$ concentration, and a $NH_3$ concentration in exhaust gases.

The exhaust gas sensor 20 is provided to generate a signal indicative of a $NH_3$ concentration in exhaust gases, a signal indicative of a $NO_x$ concentration in the exhaust gases, and a signal indicative of a $NO_2$ concentration in the exhaust gases. The exhaust gas sensor 20 includes electrolyte layers 40, 42, a porous layer 44, insulating layers 46, 47, porous layers 48, 50, a heating coil 52, a $NH_3$ Nernst cell 70, a $NO_x$ Nernst cell 72, a $NO_2$ Nernst cell 74, and a temperature sensing cell 76.

The porous layer 44 is disposed on a first side of the electrolyte layer 40. In one exemplary embodiment, the porous layer 44 is constructed from alumina. The porous layer 44 allows exhaust gases to migrate therethrough such that the exhaust gases contact the $NH_3$ sensing electrode 80, the $NO_x$ sensing electrode 90, and the $NO_2$ sensing electrode 100 disposed on the first side of the electrolyte layer 40. In one exemplary embodiment, the electrolyte layer 40 is constructed from zirconia.

The porous layer 48 has a first side that is disposed on a second side of the electrolyte layer 40. In one exemplary embodiment, the porous layer 48 is constructed from a combination of alumina and carbon black that is heated to a temperature such that only the alumina is left over. The porous layer 48 allows exhaust gases to migrate therethrough such that the exhaust gases enter a chamber 77 formed in the electrolyte layer 40, the porous layer 48, and the electrolyte layer 42. A reference electrode 82 is disposed on the second side of the electrolyte layer 40 and communicates with the chamber 77.

The electrolyte layer 42 has a first side that is disposed on a second side of the porous layer 48. In one exemplary embodiment, the electrolyte layer 42 is constructed from alumina. An impedance electrode 110 is disposed on the electrolyte layer 42 and communicates with the chamber 77.

The porous layer 50 has a first side that is disposed on a second side of the electrolyte layer 42. In one exemplary embodiment, the porous layer 48 is constructed from a combination of alumina and carbon black that is heated to a temperature such that only the alumina is left over. The porous layer 50 allows exhaust gases to migrate therethrough such that the exhaust gases enter a chamber 78 formed in the electrolyte layer 42, the porous layer 50, and the insulating layer 46. An impedance electrode 112 is disposed on the electrolyte layer 42 and communicates with the chamber 78.

The insulating layer 46 has a first side that is disposed on a second side of the porous layer 50. In one exemplary embodiment, the insulating layer 46 is constructed from alumina.

The heating coil 52 is disposed between the insulating layers 46, 47. The heating coil 52 emits heat energy in response to a voltage received from the microprocessor 22 to maintain the exhaust gas sensor 20 within a desired temperature range. In one exemplary embodiment, the insulating layer 47 is constructed from alumina.

The $NH_3$ Nernst cell 70 is provided to generate a voltage indicative of a $NH_3$ concentration in exhaust gases communicating with the $NH_3$ Nernst cell 70. The $NH_3$ Nernst cell 70 includes a $NH_3$ sensing electrode 80, the electrolyte layer 40, and the reference electrode 82. In one exemplary embodiment, the $NH_3$ sensing electrode 80 is constructed of $BiVO4$ with a dopant such as Mg, and the reference electrode is constructed of platinum. The $NH_3$ sensing electrode 80 communicates with exhaust gases passing through the porous layer 44 and the reference electrode 82 communicates with exhaust gases passing through the porous layer 48. During operation, the $NH_3$ Nernst cell 70 generates a voltage between the $NH_3$ sensing electrode 80 and the reference electrode 82 that is indicative of mainly a concentration of $NH_3$ in the exhaust gases communicating with the $NH_3$ sensing electrode 80, which is received by the microprocessor 22. In one exemplary embodiment, if there is a $NO_2$ cross interference with the $NH_3$ sensing signals of the $NH_3$ Nernst cell 70, the $NO_2$ information from the $NO_2$ cell 100 can be utilized for correcting the $NH_3$ sensing signals.

The $NO_x$ Nernst cell 72 is provided to generate a voltage indicative of a $NO_x$ concentration in exhaust gases communicating with the $NO_x$ Nernst cell 72. The $NO_x$ Nernst cell 72 includes a $NO_x$ sensing electrode 90, the electrolyte layer 40, and the reference electrode 82. In one exemplary embodiment, the $NO_x$ sensing electrode 90 is constructed from $BaFe_{12}O_{19}$ with a dopant of Boron oxide for example. The $NO_x$ sensing electrode 90 communicates with exhaust gases passing through the porous layer 44 and the reference electrode 82 communicates with exhaust gases passing through the porous layer 48. During operation, the $NO_x$ Nernst cell 72 generates a voltage between the $NO_x$ sensing electrode 90 and the reference electrode 82 that is indicative of a concentration of $NO_x$ in the exhaust gases communicating with the $NO_x$ sensing electrode 90, which is received by the microprocessor 22. The $NO_2$ concentration obtained from the $NO_2$ cell 74 is also utilized to determine the NO concentration from the $NO_x$ cell 72.

The $NO_2$ Nernst cell 74 is provided to generate a voltage indicative of a $NO_2$ concentration in exhaust gases communicating with the $NO_2$ Nernst cell 74. The $NO_2$ Nernst cell 74 includes a $NO_2$ sensing electrode 100, the electrolyte layer 40, and the reference electrode 82. The $NO_2$ sensing electrode 100 communicates with exhaust gases passing through the porous layer 44 and the reference electrode 82 communicates with exhaust gases passing through the porous layer 48. During operation, the $NO_2$ Nernst cell 74 generates a voltage between the $NO_2$ sensing electrode 100 and the reference electrode 82 that is indicative of a concentration of $NO_2$ in the exhaust gases communicating with the $NO_2$ sensing electrode 100, which is received by the microprocessor 22.

In one exemplary embodiment, the $NO_2$ sensing electrode 100 is constructed from $BaFe_{12}O_{19}$ doped on a Fe site with at least one of Ca, Co, Ga, Zn, B, Rh, Mg and Sr. In another exemplary embodiment, the $NO_2$ sensing electrode 100 is constructed from $BaFe_{12}O_{19}$ doped on a Ba site with at least one of La and Pb. For example, the $NO_2$ sensing electrode 100 can be constructed from at least one of: $BaFe_{11.5}Ca_{0.5}O_{19}$, $BaFe_{11.5}In_{0.25}Co_{0.25}O_{19}$, $BaFe_{11.5}Ga_{0.25}Co_{0.25}O_{19}$, $BaFe_{11.5}Zn_{0.5}O_{19}$, $Ba_{0.99}Pb_{0.01}Fe_{12}O_{19}$, $BaFe_{11.9}Rh_{0.1}O_{19}$, $BaFe_{11.5}B_{0.5}O_{19}$, $BaFe_{11.5}Er_{0.5}O_{19}$, $BaFe_{11.75}Mg_{0.25}O_{19}$, $BaFe_{11.5}Sr_{0.5}O_{19}$, $BaFe_{11.8}Mg_{0.15}B_{0.05}O_{19}$, $BaFe_{11.8}Mg_{0.15}Pb_{0.05}O_{19}$. It should be noted that the foregoing chemical compounds advantageously have a relatively high $NO_2$ sensing sensitivity and relatively low NO and $NH_3$ sensing sensitivity.

In another exemplary embodiment, the $NO_2$ sensing electrode 100 is constructed from $NiCr2O4$ doped with at least one dopant. For example, the $NO_2$ sensing electrode 100 can be constructed from at least one of: $NiCr_2O_4$, $NiCr_{1.95}In_{0.05}O_4$, $NiCr_{1.95}Mg_{0.05}O_4$, $NiCr_{1.95}Sb_{0.05}O_4$, $NiCr_{1.95}Ga_{0.05}O_4$, $NiCr_{1.975}Li_{0.025}O_4$, $NiCr_{1.9}Ce_{0.1}O_4$. It should be noted that the foregoing chemical compounds advantageously have a relatively high $NO_2$ sensing sensitivity and relatively low NO and $NH_3$ sensing sensitivity.

In yet another exemplary embodiment, the $NO_2$ sensing electrode 100 is constructed from at least one of $TbCrO_3$ doped with at least one dopant. For example, the $NO_2$ sensing electrode 100 can be constructed from at least one of: $TbCr_{0.96}B_{0.04}O_3$, $TbCr_{0.95}B_{0.05}O_3$, $TbCr_{0.8}B_{0.2}O_3$, $TbCr_{0.925}B_{0.075}O_3$, $TbCr_{0.975}B_{0.025}O_3$, $TbCr_{0.8}Mg_{0.14}Pb_{0.05}Co_{0.01}O_3$, $TbCr_{0.94}Ba_{0.05}B_{0.01}O_3$, $TbCr_{0.89}Ba_{0.1}Pb_{0.01}O_3$, $TbCr_{0.965}B_{0.035}O_3$, $TbCr_{0.99}Pb_{0.01}O_3$, $TbCr_{0.9}Ba_{0.05}B_{0.05}O_3$, $TbCr_{0.945}Mg_{0.05}Pb_{0.005}O_3$, $TbCr_{0.95}P_{0.05}O_3$. It should be noted that the foregoing chemical compounds advantageously have a relatively high $NO_2$ sensing sensitivity and relatively low NO and $NH_3$ sensing sensitivity.

The temperature sensing cell 76 has an impedance which is indicative of a temperature of the exhaust gas sensor 20. The temperature sensing cell 76 includes the impedance electrode 110, the electrolyte layer 42, and the impedance electrode 112. In one exemplary embodiment, the impedance electrodes 110, 112 are constructed from platinum. The microprocessor 22 is configured to measure the impedance between the impedance electrodes 110, 112 and to determine a temperature of the exhaust gas sensor 20 based on the impedance.

The microprocessor 22 is provided to receive voltages from the $NH_3$ Nernst cell 70, the $NO_x$ Nernst cell 72, and the $NO_2$ Nernst cell 74 and to determine a $NH_3$ concentration value, a $NO_x$ concentration value, and the $NO_2$ concentration value, respectively, based on the received voltages. Further, the microprocessor 22 can determine an NO concentration based on the received voltages. The microprocessor 22 is further configured to measure impedance of the temperature sensing cell 76 and to determine a temperature value based on the impedance. The microprocessor 22 is further configured to generate an output voltage that induces the heating coil 52 to emit heat energy to maintain the exhaust gas sensor 20 within a desired temperature range. The memory device 24 is configured to store concentration values and data generated by the microprocessor 22.

Figure 2:
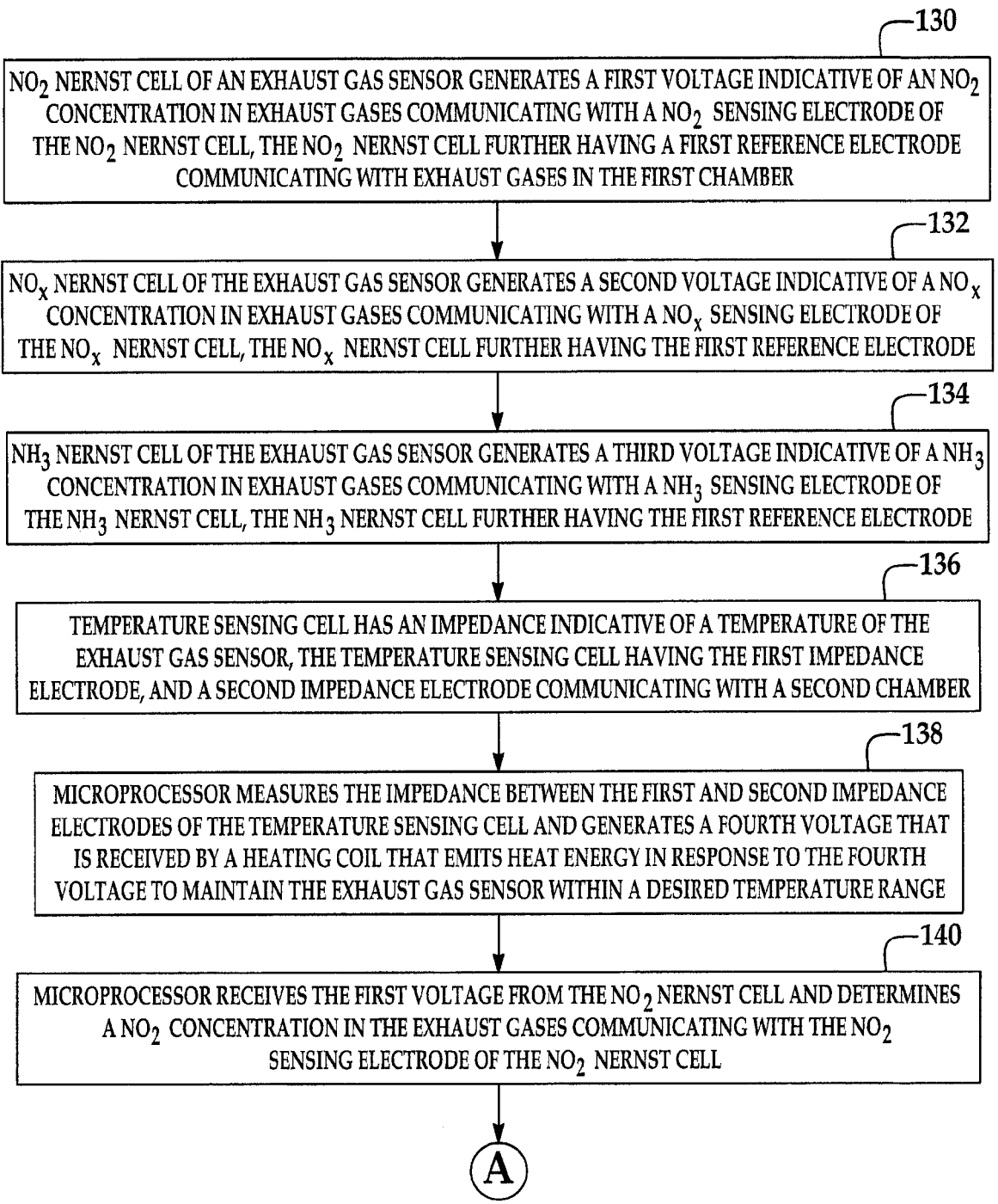
FIGS. 2-3 are flowcharts of a method for determining concentrations of exhaust gas constituents in accordance with another exemplary embodiment.
Figure 3:
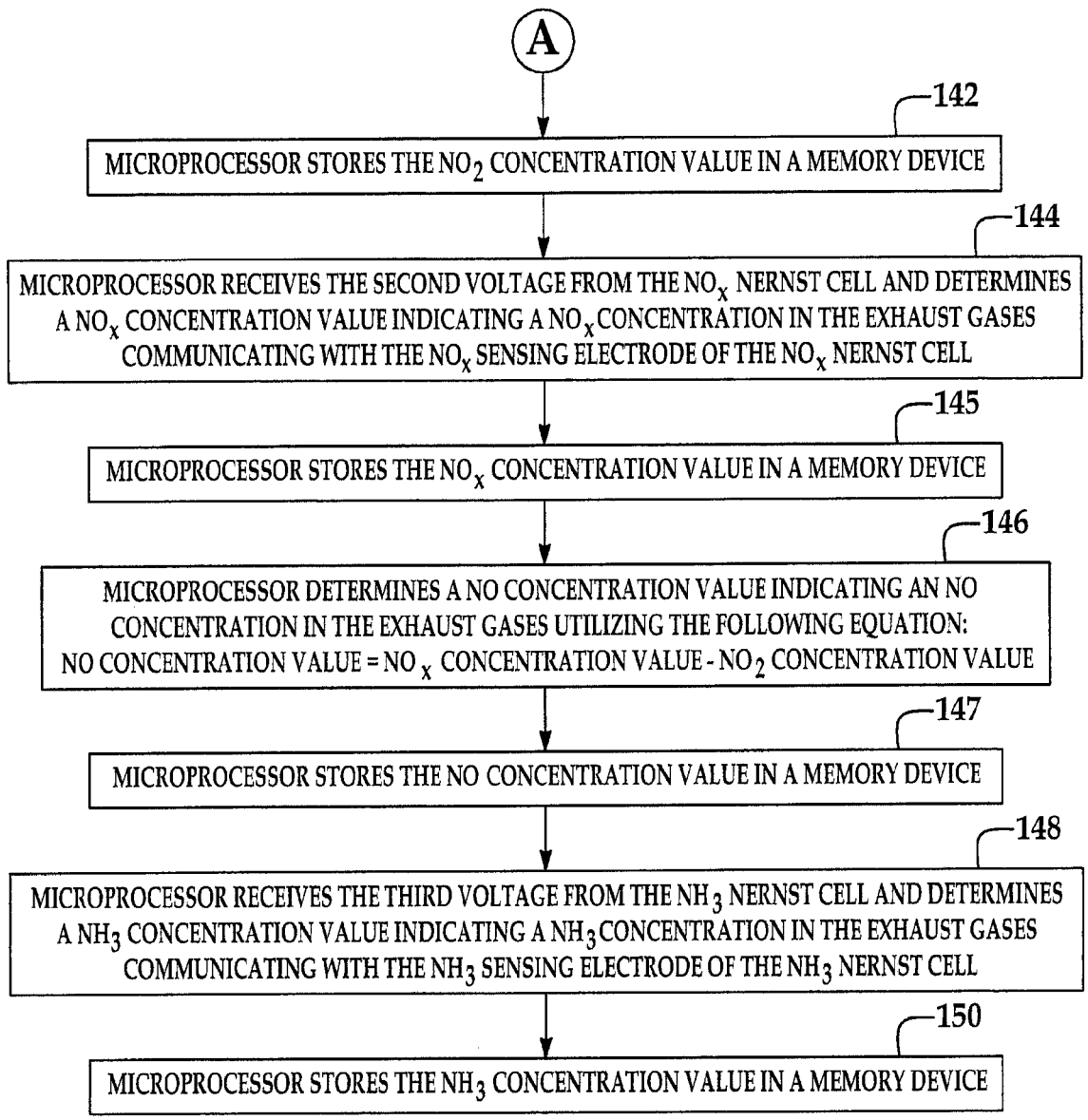

Referring to FIGS. 2 and 3, a flowchart of a method for determining concentrations of exhaust gas constituents will now be described.

At step 130, the $NO_2$ Nernst cell 74 of the exhaust gas sensor 20 generates a first voltage indicative of a $NO_2$ concentration in exhaust gases communicating with the $NO_2$ sensing electrode 100 of the $NO_2$ Nernst cell 74. The $NO_2$ Nernst cell 74 further has a reference electrode 82 communicating with exhaust gases in a chamber 77.

At step 132, the $NO_x$ Nernst cell 72 of the exhaust gas sensor 20 generates a second voltage indicative of a $NO_x$ concentration in exhaust gases communicating with the $NO_x$ sensing electrode 90 of the $NO_x$ Nernst cell 72. The $NO_x$ Nernst cell 72 further has the reference electrode 82.

At step 134, the $NH_3$ Nernst cell 70 of the exhaust gas sensor 20 generates a third voltage indicative of a $NH_3$ concentration in exhaust gases communicating with a $NH_3$ sensing electrode 80 of the $NH_3$ Nernst cell 70. The $NH_3$ Nernst cell 70 further has the reference electrode 82.

At step 136, the temperature sensing cell 76 has an impedance indicative of a temperature of the exhaust gas sensor 20. The temperature sensing cell 76 has the reference electrode 82, and the impedance electrode 112 communicating with the chamber 78.

At step 138, the microprocessor 22 measures the impedance between the impedance electrode 110, 112 of the temperature sensing cell 76 and generates a fourth voltage that is received by a heating coil that emits heat energy in response to the fourth voltage to maintain the exhaust gas sensor within a desired temperature range.

At step 140, the microprocessor 22 receives the first voltage from the $NO_2$ Nernst cell 74 and determines a $NO_2$ concentration value indicating a $NO_2$ concentration in the exhaust gases communicating with the $NO_2$ sensing electrode 100 of the $NO_2$ Nernst cell 74.

At step 142, the microprocessor 22 stores the $NO_2$ concentration value in the memory device 24.

At step 144, the microprocessor 22 receives the second voltage from the $NO_x$ Nernst cell 72 and determines a $NO_x$ concentration value indicating a $NO_x$ concentration in the exhaust gases communicating with the $NO_x$ sensing electrode 90 of the $NO_x$ Nernst cell 72.

At step 145, the microprocessor 22 stores the $NO_x$ concentration value in the memory device 24.

At step 146, the microprocessor 22 determines a NO concentration value utilizing the following equation: NO concentration value=$NO_x$ concentration value–$NO_2$ concentration value.

At step 147, the microprocessor 22 stores the NO concentration value in the memory device 24.

At step 148, the microprocessor 22 receives the third voltage from the $NH_3$ Nernst cell 70 and determines a $NH_3$ concentration value indicating the $NH_3$ concentration in the exhaust gases communicating with the $NH_3$ sensing electrode 80 of the $NH_3$ Nernst cell 70. It should be noted that the $NH_3$ concentration value can be corrected utilizing the $NO_2$ concentration value to correct for $NO_2$ cross-interference.

At step 150, the microprocessor 22 stores the $NH_3$ concentration value in the memory device 24.

The exhaust gas sensor and the method for determining concentrations of gas constituents provide a substantial advantage over other systems and methods. In particular, the exhaust gas sensor and the method provide a technical effect of accurately determining $NO_x$, $NO_2$, $NH_3$ concentrations in exhaust gases.

While embodiments of the invention are described with reference to the exemplary embodiments, it will be understood by those skilled in the art that various changes may be made and equivalents may be substituted for elements thereof without departing from the scope of the invention. In addition, many modifications may be made to the teachings of the invention to adapt to a particular situation without departing from the scope thereof. Therefore, it is intended that the invention not be limited to the embodiment disclosed for carrying out this invention, but that the invention includes all embodiments falling within the scope of the intended claims. Moreover, the use of the terms first, second, etc. does not denote any order of importance, but rather the terms first, second, etc. are used to distinguish one element from another. Furthermore, the use of the terms a, an, etc. do not denote a limitation of quantity, but rather denote the presence of at least one of the referenced items.

What is claimed is:

1. An exhaust gas sensor, comprising:
a $NO_2$ Nernst cell having a $NO_2$ sensing electrode and a first reference electrode, the first reference electrode communicating with exhaust gases in a first chamber, the $NO_2$ sensing electrode communicating with exhaust gases passing through a porous layer, the $NO_2$ Nernst cell generating a first voltage indicative of a $NO_2$ concentration in the exhaust gases communicating with the $NO_2$ sensing electrode;
a $NO_x$ Nernst cell having a $NO_x$ sensing electrode and the first reference electrode, the $NO_x$ sensing electrode communicating with the exhaust gases passing through the porous layer, the $NO_x$ Nernst cell generating a second voltage indicative of a $NO_x$ concentration in the exhaust gases communicating with the $NO_x$ sensing electrode; and
a $NH_3$ Nernst cell having a $NH_3$ sensing electrode and the first reference electrode, the $NH_3$ sensing electrode communicating with the exhaust gases passing through the porous layer, the $NH_3$ Nernst cell generating a third voltage indicative of a $NH_3$ concentration in the exhaust gases communicating with the $NH_3$ sensing electrode, wherein the $NO_2$ sensing electrode is constructed from $BaFe_{12}O_{19}$ doped on a Fe site with at least one of Ca, Co, Ga, Zn, B, Rh, Mg and Sr.

2. An exhaust gas sensor, comprising:
a $NO_2$ Nernst cell having a $NO_2$ sensing electrode and a first reference electrode, the first reference electrode communicating with exhaust gases in a first chamber, the $NO_2$ sensing electrode communicating with exhaust gases passing through a porous layer, the $NO_2$ Nernst cell generating a first voltage indicative of a $NO_2$ concentration in the exhaust gases communicating with the $NO_2$ sensing electrode;
a $NO_x$ Nernst cell having a $NO_x$ sensing electrode and the first reference electrode, the $NO_x$ sensing electrode communicating with the exhaust gases passing through the porous layer, the $NO_x$ Nernst cell generating a second voltage indicative of a $NO_x$ concentration in the exhaust gases communicating with the $NO_x$ sensing electrode; and
a $NH_3$ Nernst cell having a $NH_3$ sensing electrode and the first reference electrode, the $NH_3$ sensing electrode communicating with the exhaust gases passing through the porous layer, the $NH_3$ Nernst cell generating a third voltage indicative of a $NH_3$ concentration in the exhaust gases communicating with the $NH_3$ sensing electrode, wherein the $NO_2$ sensing electrode is constructed from $BaFe_{12}O_{19}$ doped on a Ba site with at least one of La and Pb.

3. An exhaust gas sensor, comprising:
a $NO_2$ Nernst cell having a $NO_2$ sensing electrode and a first reference electrode, the first reference electrode communicating with exhaust gases in a first chamber, the $NO_2$ sensing electrode communicating with exhaust gases passing through a porous layer, the $NO_2$ Nernst cell generating a first voltage indicative of a $NO_2$ concentration in the exhaust gases communicating with the $NO_2$ sensing electrode;
a $NO_x$ Nernst cell having a $NO_x$ sensing electrode and the first reference electrode, the $NO_x$ sensing electrode communicating with the exhaust gases passing through the porous layer, the $NO_x$ Nernst cell generating a second voltage indicative of a $NO_x$ concentration in the exhaust gases communicating with the $NO_x$ sensing electrode; and
a $NH_3$ Nernst cell having a $NH_3$ sensing electrode and the first reference electrode, the $NH_3$ sensing electrode communicating with the exhaust gases passing through the porous layer, the $NH_3$ Nernst cell generating a third voltage indicative of a $NH_3$ concentration in the exhaust gases communicating with the $NH_3$ sensing electrode, wherein the $NO_2$ sensing electrode is constructed from at least one of $BaFe_{11.5}Ca_{0.5}O_{19}$, $BaFe_{11.5}In_{0.25}Co_{0.25}O_{19}$, $BaFe_{11.5}Ga_{0.25}Co_{0.25}O_{19}$, $BaFe_{11.5}Zn_{0.5}O_{19}$, $Ba_{0.99}Pb_{0.01}Fe_{12}O_{19}$, $BaFe_{11.9}Rh_{0.1}O_{19}$, $BaFe_{11.5}B_{0.5}O_{19}$, $BaFe_{11.5}Er_{0.5}O_{19}$, $BaFe_{11.75}Mg_{0.25}O_{19}$, $BaFe_{11.5}Sr_{0.5}O_{19}$, $BaFe_{11.8}Mg_{0.15}B_{0.05}O_{19}$, $BaFe_{11.8}Mg_{0.15}Pb_{0.05}O_{19}$.

4. An exhaust gas sensor, comprising:
a $NO_2$ Nernst cell having a $NO_2$ sensing electrode and a first reference electrode, the first reference electrode communicating with exhaust gases in a first chamber, the $NO_2$ sensing electrode communicating with exhaust gases passing through a porous layer, the $NO_2$ Nernst cell generating a first voltage indicative of a $NO_2$ concentration in the exhaust gases communicating with the $NO_2$ sensing electrode;
a $NO_x$ Nernst cell having a $NO_x$ sensing electrode and the first reference electrode, the $NO_x$ sensing electrode communicating with the exhaust gases passing through the porous layer, the $NO_x$ Nernst cell generating a second voltage indicative of a $NO_x$ concentration in the exhaust gases communicating with the $NO_x$ sensing electrode; and
a $NH_3$ Nernst cell having a $NH_3$ sensing electrode and the first reference electrode, the $NH_3$ sensing electrode communicating with the exhaust gases passing through the porous layer, the $NH_3$ Nernst cell generating a third voltage indicative of a $NH_3$ concentration in the exhaust gases communicating with the $NH_3$ sensing electrode, wherein the $NO_2$ sensing electrode is constructed from $NiCr_2O_4$ doped with at least one dopant.

5. The exhaust gas sensor of claim 4, wherein the $NO_2$ sensing electrode is constructed from at least one of $NiCr_{1.95}In_{0.05}O_4$, $NiCr_{1.95}Mg_{0.05}O_4$, $NiCr_{1.95}Sb_{0.05}O_4$, $NiCr_{1.95}Ga_{0.05}O_4$, $NiCr_{1.975}Li_{0.025}O_4$, $NiCr_{1.9}Ce_{0.1}O_4$.

6. An exhaust gas sensor, comprising:
a $NO_2$ Nernst cell having a $NO_2$ sensing electrode and a first reference electrode, the first reference electrode communicating with exhaust gases in a first chamber, the $NO_2$ sensing electrode communicating with exhaust gases passing through a porous layer, the $NO_2$ Nernst cell generating a first voltage indicative of a $NO_2$ concentration in the exhaust gases communicating with the $NO_2$ sensing electrode;
a $NO_x$ Nernst cell having a $NO_x$ sensing electrode and the first reference electrode, the $NO_x$ sensing electrode communicating with the exhaust gases passing through the porous layer, the $NO_x$ Nernst cell generating a second voltage indicative of a $NO_x$ concentration in the exhaust gases communicating with the $NO_x$ sensing electrode; and
a $NH_3$ Nernst cell having a $NH_3$ sensing electrode and the first reference electrode, the $NH_3$ sensing electrode communicating with the exhaust gases passing through the porous layer, the $NH_3$ Nernst cell generating a third voltage indicative of a $NH_3$ concentration in the exhaust gases communicating with the $NH_3$ sensing electrode, wherein the $NO_2$ sensing electrode is constructed from at least one of $TbCr_{0.96}B_{0.04}O_3$, $TbCr_{0.95}B_{0.05}O_3$, $TbCr_{0.8}B_{0.2}O_3$, $TbCr_{0.925}B_{0.075}O_3$, $TbCr_{0.975}B_{0.025}O_3$, $TbCr_{0.8}Mg_{0.14}Pb_{0.05}Co_{0.01}O_3$, $TbCr_{0.94}Ba_{0.05}B_{0.01}O_3$, $TbCr_{0.89}Ba_{0.1}Pb_{0.01}O_3$, $TbCr_{0.965}B_{0.035}O_3$, $TbCr_{0.99}Pb_{0.01}O_3$, $TbCr_{0.9}Ba_{0.05}B_{0.05}O_3$, $TbCr_{0.945}Mg_{0.05}Pb_{0.005}O_3$, $TbCr_{0.95}P_{0.05}O_3$.

* * * * *